United States Patent
Arkin et al.

(10) Patent No.: US 11,633,399 B2
(45) Date of Patent: Apr. 25, 2023

(54) TREATMENT OF SKIN DISORDERS WITH COMPOSITIONS COMPRISING AN EGFR INHIBITOR

(71) Applicant: SOL-GEL TECHNOLOGIES LTD., Ness Ziona (IL)

(72) Inventors: Moshe Arkin, Kfar Shmaryahu (IL); Marcel Zighelboim, Kiriat Motzkin (IL); Ori Nov, Tarum (IL); Ofer Toledano, Kfar Saba (IL); Karine Neimann, Ness Ziona (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 16/737,503

(22) Filed: Jan. 8, 2020

(65) Prior Publication Data

US 2020/0197397 A1    Jun. 25, 2020

Related U.S. Application Data

(63) Continuation-in-part of application No. PCT/IL2019/051410, filed on Dec. 25, 2019.

(60) Provisional application No. 62/877,957, filed on Jul. 24, 2019, provisional application No. 62/877,990, filed on Jul. 24, 2019, provisional application No. 62/784,738, filed on Dec. 25, 2018.

(51) Int. Cl.
| | |
|---|---|
| A61K 31/505 | (2006.01) |
| A61K 31/517 | (2006.01) |
| A61K 31/5377 | (2006.01) |
| A61K 39/395 | (2006.01) |
| A61K 9/00 | (2006.01) |
| A61K 45/06 | (2006.01) |
| A61K 31/05 | (2006.01) |
| A61K 9/06 | (2006.01) |
| A61K 31/506 | (2006.01) |

(52) U.S. Cl.
CPC .......... *A61K 31/517* (2013.01); *A61K 9/0014* (2013.01); *A61K 9/06* (2013.01); *A61K 31/05* (2013.01); *A61K 31/506* (2013.01); *A61K 31/5377* (2013.01); *A61K 39/3955* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,968,579 B2 * | 5/2018 | Lu | ......................... A61K 31/197 |
| 2002/0045630 A1 | 4/2002 | Arnold et al. | |
| 2003/0013681 A1 | 1/2003 | Chang et al. | |
| 2004/0033207 A1 | 2/2004 | Kang et al. | |
| 2006/0205757 A1 | 9/2006 | Zhang et al. | |
| 2007/0238718 A1 | 10/2007 | Grauert et al. | |
| 2007/0238730 A1 | 10/2007 | Breitfelder et al. | |
| 2007/0238746 A1 | 10/2007 | Brandl et al. | |
| 2007/0244104 A1 | 10/2007 | Brandl et al. | |
| 2007/0259855 A1 | 11/2007 | Maier et al. | |
| 2009/0318446 A1 | 12/2009 | Fischer et al. | |
| 2010/0029709 A1 | 2/2010 | Menet et al. | |
| 2010/0129357 A1 | 5/2010 | Garcia-Martinez et al. | |
| 2010/0150829 A1 | 6/2010 | Garcia-Martinez et al. | |
| 2011/0201608 A1 | 8/2011 | Hoffmann et al. | |
| 2011/0250201 A1 | 10/2011 | Smith | |
| 2011/0263549 A1 | 10/2011 | Fiegen et al. | |
| 2012/0028939 A1 | 2/2012 | Hoffmann et al. | |
| 2013/0023502 A1 | 1/2013 | Dahmann et al. | |
| 2013/0029949 A1 | 1/2013 | Hoffmann et al. | |
| 2013/0183264 A1 | 7/2013 | Smith | |
| 2013/0281430 A1 | 10/2013 | Dahmann et al. | |
| 2014/0271459 A1 | 9/2014 | Dutzar et al. | |
| 2014/0271540 A1 | 9/2014 | Stogniew et al. | |
| 2014/0275025 A1 | 9/2014 | Anderskewitz et al. | |
| 2014/0303140 A1 | 10/2014 | Desroy et al. | |
| 2015/0005340 A1 | 1/2015 | Gong | |
| 2015/0056192 A1 | 2/2015 | Chaturvedi et al. | |
| 2016/0022674 A1 | 1/2016 | Steggerda et al. | |

(Continued)

FOREIGN PATENT DOCUMENTS

| | | |
|---|---|---|
| AU | 2017203536 A1 | 6/2017 |
| CN | 102438653 A | 5/2012 |

(Continued)

OTHER PUBLICATIONS

Kaftan et al. Delay of tympanic membrane wound healing in rats with topical application of a tyrosine kinase inhibitor, Wound Repair Regen.16(3):364-9,May-Jun. 2008, Abstract only.*

(Continued)

*Primary Examiner* — Claire Kaufman

(74) *Attorney, Agent, or Firm* — Mark S. Cohen; Pearl Cohen Zedek Latzer Baratz LLP

(57) ABSTRACT

This invention relates to compositions and methods of treatment of skin or mucosal disorders by administration of compositions comprising at least one EGFR inhibitor, such as topical compositions comprising erlotinib. The compositions of this invention are useful for the treatment, prevention or amelioration of skin or mucosal disorders like psoriasis, palmoplantar psoriasis, acquired palmoplantar keratosis, eczema, ichtyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa.

21 Claims, No Drawings

(56) References Cited

U.S. PATENT DOCUMENTS

| | | |
|---|---|---|
| 2016/0067241 A1 | 3/2016 | Brown |
| 2016/0074337 A1 | 3/2016 | Brown |
| 2016/0244446 A1 | 8/2016 | Dahmann et al. |
| 2017/0073333 A1 | 3/2017 | Hoffmann et al. |
| 2017/0151264 A1 | 6/2017 | Godessart Marina et al. |
| 2018/0016312 A1 | 1/2018 | Bel Aiba et al. |
| 2018/0208594 A1 | 7/2018 | Jacobsen et al. |
| 2019/0175491 A1* | 6/2019 | Abraham ............... A61K 47/08 |

FOREIGN PATENT DOCUMENTS

| | | |
|---|---|---|
| CN | 102740888 A | 10/2012 |
| WO | WO-2009091889 A1 | 7/2009 |
| WO | WO-2010065072 A1 | 6/2010 |
| WO | WO-2011066369 A2 | 6/2011 |
| WO | WO-2011066371 A2 | 6/2011 |
| WO | WO-2011066374 A2 | 6/2011 |
| WO | WO-2012071554 A2 | 5/2012 |
| WO | WO-2012071561 A2 | 5/2012 |

OTHER PUBLICATIONS

Williams et al., Emerging research in chronic pruritus: from bedside to bench and back again, Medicines, 7, 24, Apr. 29, 2020.*
Powell et al., Growth inhibition of psoriatic keratinocytes by quinazoline tyrosine kinase inhibitors, Bri. J. Dermatol. 141:802-810, 1999.*
Smith et al., Tapinarof is a natural AhR agonist that rsolves skin inflammation in mice and humans, J. Invest. Dermatol. 137:2110-2119, Aug. 2017.*
Papp et al., Treatment of plaque psoriasis with an ointment formulation of the Janus kinase inhibitor, tofacitinib_ a Phase 2b randomized clinical trial, BMC Dermatol. 16:15, 2016.*
Lernia et al.,Tofacitinib in the treatment of chronic plaque psoriasis,Drug Design Develop. Thera. 10:553-559, 2016.*
Kaidbey KH, Petrozzi JW, Kligman AM. Treatment of Psoriasis With Topically Applied Tretinoin and Steroid Ointment. Arch Dermatol.111(8):1001-1003, Abtract only, 1975.*
Oyama et al., A case of rapid improvement of severe psoriasis during molecular-targeted therapy using an epidermal growth factor receptor tyrosine kinase inhibitor for metastatic lung adenocarcinoma, J. Am. Acad. Dermaol. 66(6):e251, 2011.*
Lee et al., Treatment of Keratin 16 Palmoplantar Keratoderma with Topical Erlotinib, JAMA Dermatol. 158(2):216-217, Feb. 2022.*
Ngyuen et al., Stability and Formulation of Erlotinib in Skin Creams, Molecules, 27, 1070, 9 pages. https://doi.org/10.3390/molecules27031070, 2022.*
Ranson et al., A phase I dose-escalation and bioavailability study of oral and intravenous formulations of erlotinib (Tarceva®, OSI-774) in patients with advanced solid tumors of epithelial origin, Canc. Chemother. Pharmacol. 66(1):53-58, 2010.*
Nishmura et al., Effect of the molecular targeted drug, erlotinib, against endometrial cancer expressing high levels of epidermal growth factor receptor, BMC Canc. 15:957, 11 pages, DOI 10.1186/s12885-015-1975-5, 2015.*
Goepel et al., Rapid improvement of psoriasis in a patient with lung cancer after treatment with erlotinib, J. Eur. Acad. Dermatol. Venereol. 32(8):e311-e313, Feb. 11, 2018.*
Leprieur et al., Improvementof psoriasis in a lung cancer patient treated with erlotinib, Eur. J. Dermatol. 20(2):243-244, Mar.-Apr. 2010.*
Wierzicka et al., Improvement of psoriasis and cutaneous side-effects during tyrosine kinase inhibitor therapy for renal metastatic adenocarcinoma. A role for epidermal growth factor receptor (EGFR) inhibitors in psoriasis ? Br. J. Dermatol. 155: 213-214, 2006.*
DrugBank Online, Trentinoin, Retrieved online from: <URL:https://go.drugbank.com/drugs/DB00755>, [retrieved onilne Jun. 3, 2022], Jun. 3, 2022.*
Office of Drug Evauliation, FDA, Pharmacology Review: Application No. 205437Orig1s000PharmR , Retrieved online from, <URL: https://www.accessdata.fda.gov/drugsatfda_docs/nda/2014/205437Orig1s000PharmR.pdf>, [retrieved online Jun. 3, 2022], Mar. 13, 2014.*
Trivin et al., Complete sustained regression of extensive psoriasis with cetuximab combination chemotherapy. Acta Oncol. 43(6): 592-593, 2004.*
Kamaria et al., Eruptive cutaneous squamous cell carcinoma and psoriasis: response to cetuximabClin. Exp. Dermatol. 39:604-607, 2014, abstract only.*
Akiyama, M., Takeichi, T., McGrath, J. A., & Sugiura, K. (2018). Autoinflammatory keratinization diseases: an emerging concept encompassing various inflammatory keratinization disorders of the skin. Journal of dermatological science, 90(2), 105-111.
Alavi, A., Anooshirvani, N., Kim, W. B., Coutts, P., & Sibbald, R. G. (2015). Quality-of-life impairment in patients with hidradenitis suppurativa: a Canadian study. American journal of clinical dermatology, 16(1), 61-65.
Alexandrescu, D. T., Dasanu, C. A., Farzanmehr, H., & Kauffman, C. L. (2008). Development of squamous cell carcinomas in Darier disease: a new model for skin carcinogenesis?. British Journal of Dermatology, 159(6), 1378-1380—Abstract.
Amini, S., Viera, M. H., Valins, W., & Berman, B. (2010). Non-surgical innovations in the treatment of nonmelanoma skin cancer. The Journal of clinical and aesthetic dermatology, 3(6), 20:34.
Basset-Séguin, N. (Dec. 2011). What's new in dermato-oncology?. In Annales de dermatologie et de venereologie (vol. 138)—Article in French—Abstract in English.
Ben-Bassat, H., & Klein, B. Y. (2000). Inhibitors of tyrosine kinases in the treatment of psoriasis. Current pharmaceutical design, 6(9), 933-942.
Chen, K. L., Lin, C. C., Cho, Y. T., Yang, C. W., Sheen, Y. S., Tsai, H. E., & Chu, C. Y. (2016). Comparison of Skin Toxic Effects Associated With Gefitinib, Erlotinib, or Afatinib Treatment for Non-Small Cell Lung Cancer. JAMA dermatology, 152(3), 340-342.
Curry, J. L., Torres-Cabala, C. A., Kim, K. B., Tetzlaff, M. T., Duvic, M., Tsai, K. Y., . . . & Prieto, V. G. (2014). Dermatologic toxicities to targeted cancer therapy: shared clinical and histologic adverse skin reactions. International journal of dermatology, 53(3), 376-384—Abstract.
Dev, T., Mahajan, V. K., & Sethuraman, G. (2019). Hereditary palmoplantar keratoderma: A practical approach to the diagnosis. *Indian dermatology online journal*, 10(4), 365.
Dimitroff, C. J., Klohs, W., Sharma, A., Pera, P., Driscoll, D., Veith, J., . . . & Henderson, B. (1999). Anti-angiogenic activity of selected receptor tyrosine kinase inhibitors, PD166285 and PD173074: implications for combination treatment with photodynamic therapy. Investigational new drugs, 17(2), 121-135.
Ehmann, L. M., Ruzicka, T., & Wollenberg, A. (2011). Cutaneous side-effects of EGFR inhibitors and their management. Skin Therapy Lett, 16(1), 1-3.
Escudero-Góngora, M. M., Del Pozo-Hernando, L. J., Corral-Magaña, O., & Antón, E. (2018). Inflammation of Actinic Keratosis During Panitumumab Therapy. Actas dermo-sifiliograficas, 109(8), 749.
Guy, R., Green, M. R., & Kealey, T. (1996). Modeling acne in vitro. Journal of investigative dermatology, 106(1), 176-182.
Hermanns, J. F., Piérard, G. E., & Quatresooz, P. (2007). Erlotinib-responsive actinic keratoses. Oncology reports, 18(3), 581-584.
Jenni, D., Karpova, M. B., Mühleisen, B., Mangana, J., Dreier, J., Hafner, J., & Dummer, R. (2016). A prospective clinical trial to assess lapatinib effects on cutaneous squamous cell carcinoma and actinic keratosis. ESMO open, 1(1), e000003.
Joseph, S. R., Endo-Munoz, L., Gaffney, D. C., Saunders, N. A., & Simpson, F. (2015). Dysregulation of epidermal growth factor receptor in actinic keratosis and squamous cell carcinoma. In Actinic Keratosis (vol. 46, pp. 20-27). Karger Publishers.
Kanitakis, J., Lora, V., Chouvet, B., Zambruno, G., Haftek, M., & Faure, M. (2011). Circumscribed palmo-plantar hypokeratosis: a disease of desquamation? Immunohistological study of five cases and literature review. Journal of the European Academy of Dermatology and Venereology, 25(3), 296-301—Abstract.

(56) References Cited

OTHER PUBLICATIONS

Kato, S., Lippman, S. M., Flaherty, K. T., & Kurzrock, R. (2016). The conundrum of genetic "drivers" in benign conditions. Journal of the National Cancer Institute, 108(8), djw036.

Kenner-Bell, B. M., Paller, A. S., & Lacouture, M. E. (2010). Epidermal growth factor receptor inhibition with erlotinib for palmopiantar keratoderma. Journal of the American Academy of Dermatology, 63(2), e58-e59.

Kiyohara, Y., Yamazaki, N., & Kishi, A. (2013). Erlotinib-related skin toxicities: treatment strategies in patients with metastatic non-small cell lung cancer. Journal of the American Academy of Dermatology, 69(3), 463-472.

Krähn, G., Greulich, K. M., Bezold, G., Dieterle, C., Wolff, H., & Peter, R. U. (1999). Receptor tyrosine kinase and p16/CDKN2 expression in a case of tripe palms associated with non-small-cell lung cancer. Dermatology, 199(4), 290-295.

Kwon, E. J., Kish, L. S., & Jaworsky, C. (2009). The histologic spectrum of epithelial neoplasms induced by sorafenib. Journal of the American Academy of Dermatology, 61(3), 522-527—Abstract.

Li, S., Zhan, H., & Peng, S. (2008). Expression of epidermal growth factor receptor Ki67 and p16 in human middle ear cholesteatoma. Lin chuang er bi yan hou tou jing wai ke za zhi= Journal of clinical otorhinolaryngology, head, and neck surgery, 22(21)—Article in Chinese—Abstract in English.

Liu, W., Ren, H., Ren, J., Yin, T., Hu, B., Xie, S., . . . & Xie, D. (2013). The role of EGFR/PI3K/Akt/cyclinD1 signaling pathway in acquired middle ear cholesteatoma. Mediators of inflammation, 2013.

Lu, J., Goldstein, K. M., Chen, P., Huang, S., Gelbert, L. M., & Nagpal, S. (2005). Transcriptional profiling of keratinocytes reveals a vitamin D-regulated epidermal differentiation network. Journal of investigative dermatology, 124(4), 778-785.

Miceli, A., & Schmieder, G. J. (2019). Palmopiantar psoriasis. In StatPearls [Internet]. StatPearls Publishing. Retrieved on-line at https://www.ncbi.nlm.nih.gov/books/NBK448142/.

Morse, L., & Calarese, P. (Aug. 2006). EGFR-targeted therapy and related skin toxicity. In Seminars in oncology nursing (vol. 22, No. 3, pp. 152-162). WB Saunders—Abstract.

Neyns, B., Meert, V., & Vandenbroucke, F. (2008). Cetuximab treatment in a patient with metastatic colorectal cancer and psoriasis. Current Oncology, 15(4), 196.

Okereke, U. R., Colozza, S., & Cohen, D. E. (2014). A case of new onset keratosis pilaris after discontinuation of erlotinib. Journal of drugs in dermatology: JDD, 13(11), 1410-1411—Abstract.

Overbeck, T. R., & Griesinger, F. (2012). Two cases of psoriasis responding to erlotinib: time to revisiting inhibition of epidermal growth factor receptor in psoriasis therapy?. Dermatology, 225(2), 179-182.

PCT International Search Report and Written Opinion dated Feb. 20, 2020, issued in parent Application No. PCT/IL2019/051410, dated Dec. 25, 2019.

Tan, F., Yang, G., Wang, Y., Chen, H., Yu, B., Li, H., . . . & Ding, L. (2018). Icotinib inhibits EGFR signaling and alleviates psoriasis-like symptoms in animal models. Biomedicine & Pharmacotherapy, 98, 399-405.

Taute, S., Pfister, H. J., & Steger, G. (2017). Induction of tyrosine phosphorylation of UV-activated EGFR by the beta-human papillomavirus type 8 E6 leads to papillomatosis. Frontiers in microbiology, 8, 2197.

Uribe, P., & Gonzalez, S. (2011). Epidermal growth factor receptor (EGFR) and squamous cell carcinoma of the skin: molecular bases for EGFR-targeted therapy. Pathology—Research and Practice, 207(6), 337-342—Abstract.

Wollenberg, A., Kroth, J., Hauschild, A., & Dirschka, T. (2010). Cutaneous side effects of EGFR inhibitors—appearance and management. Deutsche medizinische Wochenschrift (1946), 135(4)—Article in German—Abstract in English.

Wollina, U. (2014). Update of cetuximab for non-melanoma skin cancer. Expert opinion on biological therapy, 14(2), 271-276.

Xie, S., Xiang, Y., Wang, X., Ren, H., Yin, T., Ren, J., & Liu, W. (2016). Acquired cholesteatoma epithelial hyperproliferation: roles of cell proliferation signal pathways. The Laryngoscope, 126(8), 1923-1930—Abstract.

Zhao, J., Zhang, X., Chen, Z., & Wu, J. H. (2016). Case report: Bazex syndrome associated with pulmonary adenocarcinoma. Medicine, 95(2).

International Preliminary Report on Patentability (Chapter 1 of the PCT) dated Jul. 8, 2021, for the corresponding PCT International Application No. PCT/IL2019/051410, dated Dec. 25, 2019.

Bissonnette, R. et al. (2012). Efficacy and safety of topical WBI-1001 in patients with mild to moderate psoriasis: results from a randomized double-blind placebo-controlled, phase II trial. *Journal of the European Academy of Dermatology and Venereology*, 26(12), 1516-1521.

Mas-Vidal, A. et al. (2011). Psoriasis induced by cetuximab: A paradoxical adverse effect. *Australasian Journal of Dermatology*, 52(1), 56-58.

Selam, M. (2013). Psoriasis aggravation due to lapatinib. *BMJ Case Reports*, 2013, bcr2012007592, 1-3.

Zorzou, M. P. et al. (2004). Exacerbation of psoriasis after treatment with an EGFR tyrosine kinase inhibitor [1]. *Acta Dermato-Venereologica*, 84(4), 308-309.

* cited by examiner

TREATMENT OF SKIN DISORDERS WITH COMPOSITIONS COMPRISING AN EGFR INHIBITOR

CROSS REFERENCE TO RELATED APPLICATIONS

This application is a Continuation-in-Part Application of PCT International Patent Application No. PCT/IL2019/051410 filed on Dec. 25, 2019, which claims the benefit of U.S. Provisional Application Ser. No. 62/784,738, filed on Dec. 25, 2018, of U.S. Provisional Application Ser. No. 62/877,990, filed on Jul. 24, 2019 and U.S. Provisional Application Ser. No. 62/877,957 filed Jul. 24, 2019, which are all incorporated in their entirety herein by reference.

FIELD OF THE INVENTION

This invention, in some embodiments thereof, relates to compositions and methods of treatment of skin or mucosal disorders by administration of compositions comprising at least one EGFR inhibitor, such as topical compositions comprising erlotinib. The compositions of this invention are useful for the treatment, prevention or amelioration of skin or mucosal disorders like psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa.

BACKGROUND

Epidermal Growth Factor Receptor (EGFR) inhibitor drugs like erlotinib, gefitinib, osimertinib and brigatinib target the EGFR (a known oncogene) and are used for the systemic treatment of some forms of cancer (lung, colon).

There is no US-marketed EGFR inhibitor drug for topical use or for injection. The EGFR inhibitor erlotinib is sold as oral tablets (Tarceva). Similarly, gefitinib (Iressa), osimertinib (Tigresso) and brigatinib (Alunbrig) are sold as oral tablets.

There is an unmet need for methods of topical or injectable treatment of skin or mucosal disorders like psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa.

SUMMARY OF THE INVENTION

In one embodiment, this invention is directed to a topical composition for treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w.

In one further embodiment, this invention is directed to a topical composition for treatment, prevention or alleviation of a hyperkeratinization disorder in a patient in need thereof, comprising about 0.75% w/w erlotinib hydrochloride and from about 10% to about 98% w/w at least one penetration enhancer, wherein the composition is formulated as a gel.

In one further embodiment, this invention is directed to a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w tapinarof and from about 10% to about 98% w/w at least one penetration enhancer.

In one further embodiment, this invention is directed to a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w tofacitinib citrate and from about 10% w/w to about 98% w/w at least one penetration enhancer.

In one further embodiment, this invention is directed to a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w apremilast and from about 10% w/w to about 98% w/w at least one penetration enhancer.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of (i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and (ii) a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w, wherein the two separate compositions are administered concomitantly or sequentially, in either order.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a composition comprising:

(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and (ii) at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w.

In another embodiment, the method further comprises administering a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of (i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and (ii) a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof; in a concentration of from about 0.01% to about 1%, from about 1% to about 3%, from about 3% to about 5% w/w, wherein the two separate compositions are administered concomitantly or sequentially, in either order.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of
a composition comprising:

(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and (ii) at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof; in a concentration of from about 0.01% to about 1%, from about 1% to about 3%, from about 3% to about 5% w/w.

In another embodiment, the method further comprises administering a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of (i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w;
(ii) a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w; and
(iii) a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof in a concentration of from about 0.01% to about 1%, from about 1% to about 3%, from about 3% to about 5% w/w;
wherein the three separate compositions are administered concomitantly or sequentially, in either order.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of
a composition comprising:
(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w;
(ii) at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w; and
(iii) at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3%, from about 3% to about 5% w/w.

DETAILED DESCRIPTION OF THE INVENTION

Treatment with EGFR inhibitors in general and erlotinib in particular is known to induce cutaneous conditions like acneiform rash, papulopustular rash, abnormal scalp hair growth, abnormal facial hair growth, abnormal hair growth, abnormal eyelash growth, paronychia with or without pyogenic granulomas and telangiectasia.

This is probably one of the reasons that no topical EGFR inhibitor product is marketed so far. A number of clinical studies are underway on the topical treatment or prevention of the EGFR inhibitors-induced cutaneous side-effects, but none on treatment of skin disorders by administration of topical EGFR inhibitors.

It occurred to the present inventors that EGFR inhibitors, being tyrosine kinase inhibitors and also essential regulators of multiple epidermal functions have the potential to prevent, cure or alleviate a number of skin or mucosal disorders in which tyrosine kinase inhibition or epidermal function regulation play a causal mechanistic role. In addition, there are advantages in topically treating skin disorders by topical or injectable instead of systemic administration, thus avoiding systemic side-effects, provided the cutaneous EGFR inhibitors' side-effects can be avoided, prevented or minimized.

The EGFR inhibitor cutaneous side-effects reported in the medical literature are the result of oral (systemic) treatment with EGFR inhibitors. The compositions and methods of treatment of this invention use non-oral administration, thus avoiding systemic effects, and are therefore expected to present an advantageous cutaneous side-effects profile as compared to the EGFR inhibitor oral products.

Some of the skin or mucosal disorders contemplated for treatment with the methods of this invention are psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa (see below).

Psoriasis

Psoriasis is characterized inter alia by epidermal hyperproliferation. Protein tyrosine kinases (PTKs) regulate cell proliferation, differentiation and immune processes. Uncontrolled signaling from receptor and intracellular tyrosine kinases can lead to numerous proliferative diseases, i.a. psoriasis (Ben-Bassat H et al Curr. Pharm Des. 2000 June; 6(9):933-42).

Palmoplantar Psoriasis

Palmoplantar psoriasis is a variant of psoriasis that characteristically affects the skin of the palms and soles. It features hyperkeratotic, pustular, or mixed morphologies. The condition is chronic in nature and produces significant functional disability (see Miceli A, Schmieder G J. Palmoplantar Psoriasis. [Updated 2019 Jun. 3]. StatPearls [Internet]. Treasure Island (FL): StatPearls Publishing; 2019 January).

Non-Melanoma Skin Cancer (NMSC)

Skin cancers include three main types—basal-cell skin cancer (BCC), squamous cell skin cancer (SCC) and melanoma.

The first two types together (BCC and SCC) are known as non-melanoma skin cancers (NMSC).

Cetuximab (Erbitux), an EGFR inhibitor, has been investigated for oral treatment of NMSC (Wollina U., Expert Opinion on Biological Therapy, Vol. 14, 2014—Issue 2).

Uncontrolled signaling from receptor and intracellular tyrosine kinases can lead to numerous proliferative diseases, i.e. cancer (Ben-Bassat H et al Curr. Pharm Des. 2000 June; 6(9):933-42).

Actinic Keratosis (AK)

Dysregulation of the EGFR signaling results in cellular hyperproliferation and defects in differentiation (Joseph S R et al., "Dysregulation of epidermal growth factor receptor in actinic keratosis and squamous cell carcinoma", Curr Probl. Dermatol. 2015; 46:20-7).

Gorlin Syndrome (NBCCS)

NBCCS (Nevoid Basal-Cell Carcinoma Syndrome) is i.e. a predisposition for BCC caused by a genetic mutation. Oral treatment of NMSC (which includes BCC) with cetuximab (an EGFR inhibitor) has been investigated, but the topical treatment of Gorlin syndrome with topical EGFR inhibitors was never attempted.

Hidradenitis Suppurativa (HS)

Hidradenitis suppurativa (HS), also known as acne inversa, is a long-term chronic skin disease whose present treatment options are often unsatisfactory. HS has a profound effect on patient's quality of life (QoL). Alavi A. et al., reviewed QoL aspects of this disease in an article titled "Quality-of-Life Impairment in Patients with Hidradenitis Suppurativa" (Am J Clin Dermatol, 2014, vol. 15. No. 6).

The clinical picture of HS includes solitary nodules, diffuse, painful abscesses, malodorous drainage, sinus tract formation and scarring.

The exact cause of hidradenitis suppurativa is still unclear, but it is believed that the underlying mechanism involves dysfunction of the apocrine sweat glands or hair follicles.

Pachyonychia Congenita

Pachyonychia Congenita (PC) is an ultra-rare genetic autosomal dominant skin disorder. PC is caused by a mutation in one of five keratin genes KRT6A, KRT6B, KRT6C, KRT16 or KRT17. Keratin genes are responsible for production of keratins, which are tough, fibrous proteins that form filaments to support skin cells and give them shape and strength. Keratin filaments help cells handle pressure and stretching. With PC, the filaments do not form properly, causing extreme cell fragility. PC is a congenital autosomal dominant syndrome primarily affecting males, mainly characterized by increased thickness of the nails, hyperkeratosis involving the palms, soles, knees, and elbows, with popular tiny cutaneous horns, leukoplakia of the mucous membranes (leukokeratosis of the oral mucosa), and usually excessive sweating of the hands and feet; associated with development of bullae on palms and soles after trauma, also characterized by cysts of various types (including steatocystoma and pilosebaceous cysts), characterized by follicular hyperkeratosis (FHK or bumps around hairs at friction sites such as waist, hips, knees, elbows). Most common in children and lessens after teenage years.

In some embodiments, the PC is associated with nail dystrophy. In other embodiments the PC is associated with a keratinization skin disorder.

Keratinization Skin Disorders

This class of skin disorders includes hyperkeratinization disorder, Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, pityriasis rubra pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome.

A new terminology for the keratinization skin disorders has been recently introduced (see Akiyama M. et al., J Dermatol Sci. 2018 May; 90(2):105-111, "Autoinflammatory keratinization diseases: An emerging concept encompassing various inflammatory keratinization disorders of the skin").

In one embodiment the keratinization skin disorder includes Pachyonychia Congenita (PC).

Keratinization Mucosal Disorders

This class of mucosal (oral, vaginal, anal) disorders includes Lichen Planus, Leukoplakia and Lichen sclerosus.

Prurigo Nodularis

Prurigo nodularis is a skin disease characterised by pruritic (itchy) nodules which usually appear on the arms or legs. Patients often present with multiple excoriated lesions caused by scratching. Prurigo nodularis is very hard to treat, but current therapies include steroids, vitamins, cryosurgery, thalidomide and UVB light.

Prurigo Pigmentosa

Prurigo pigmentosa is a rare skin condition of unknown cause, characterized by the sudden onset of erythematous papules that leave a reticulated hyperpigmentation when they heal.

In some embodiments, the EGFR inhibitor in this invention is selected from gefitinib, erlotinib, lapatinib, cetuximab, panitumumab, vandetanib, necitumumab, osimertinib and combinations thereof.

According to some embodiments, there are provided novel methods of treatment of above enumerated skin or mucosal disorders by topical administration of at least one EGFR inhibitor.

In some embodiments there is provided a method of treatment of a skin or mucosal disorder in which epidermal function regulation or tyrosine kinase inhibition play a causal mechanistic role, by topical administration of a therapeutically effective amount of at least one EGFR inhibitor.

According to some embodiments, there is provided a topical composition for treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa, comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w. In another embodiment, the keratinization skin disorder is hyperkeratinization disorder. Each possibility represents a separate embodiment of this invention. In some embodiments, the topical composition further comprises at least one penetration enhancer. In one embodiment, the penetration enhancer is in a concentration of between 10% w/w to about 98% w/w of said composition. In one other embodiment, the at least one penetration enhancer is selected from: DMSO (dimethyl sulfoxide), ethanol, isopropyl alcohol, dimethyl isosorbide, isopropyl myristate, oleic acid, a polyethylene glycol, hexylene glycol, glycofurol and combinations thereof. In one another embodiment, the at least one penetration enhancer has dual functionality and may act also as solvent. Each possibility represents a separate embodiment of this invention.

In some embodiments, the topical composition further comprises at least one solvent. In one embodiment, the at least one solvent is selected from DMSO (dimethylsulfoxide), ethanol, isopropyl alcohol, propylene glycol, dimethyl isosorbide, isopropyl myristate, oleic acid, a polyethylene glycol, hexylene glycol, glycerin, glycofurol and combinations thereof. Each possibility represents a separate embodiment of this invention.

In some embodiments, the topical composition further comprises at least one additional active agent. In some embodiments, the topical composition further comprises at least one additional first active agent (in combination with the EGFR inhibitor; or in combination with the EGFR inhibitor and the at least second active agent) and the first active agent, or as combination with the EGFR inhibitor) selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w. Each possibility represents a separate embodiment of this invention.

In some embodiments, the topical composition further comprises at least one additional second active agent (in combination with the EGFR inhibitor; or in combination with the EGFR inhibitor and the at least first active agent) selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3% or from about 3% to about 5% w/w. Each possibility represents a separate embodiment of this invention.

In some embodiments, the at least one additional active agent is tapinarof, in a concentration of from about 0.01% to about 1%, from about 1% to about 3%, from about 3% to about 5% w/w.

In some embodiments, the topical composition further comprises at least one ingredient selected from a moisturizer, a skin barrier, urea, ammonium lactate and combinations thereof, in a concentration of from about 0.01% w/w to about 1% w/w, from about 1% w/w to about 3% w/w or from about 3% w/w to about 5% w/w.

In some embodiments, the at least one EGFR inhibitor is selected from erlotinib, gefitinib, lapatinib, their salts, hydrates or solvates and combinations thereof. In one embodiment, the at least one EGFR inhibitor is erlotinib hydrochloride.

In some embodiments, the at least one PDE4 inhibitor is selected from roflumilast, apremilast, piclamilast, ibudliast, cilomilast their salts, hydrates or solvates and combinations thereof.

In some embodiments, the Janus kinase inhibitor (JAK inhibitor) is selected from tofacitinib, abrocitinib, ruxolitinib, delgocitinib, oclacitinib, baricitinib, peficitinib, or salt thereof and combinations thereof. In another embodiment, the Janus kinase inhibitor (JAK inhibitor) is tofacitinib or salt thereof. In another embodiment, the Janus kinase inhibitor (JAK inhibitor) is tofacitinib citrate.

Some of the above additional active agents, selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, play the role of avoiding, preventing or alleviating the EGFR inhibitor cutaneous side-effects.

According to some embodiments, the topical composition of this invention is a cream, an ointment, a gel, a lotion, a spray, a shampoo, a patch or a foam.

In one embodiment, the at least one EGFR inhibitor is erlotinib hydrochloride and the composition is formulated as a topical gel.

In one embodiment, there is provided a topical composition for treatment, prevention or alleviation of a hyperkeratinization disorder in a patient in need thereof, comprising about 0.75% w/w erlotinib hydrochloride and from about 10% to about 98% w/w at least one penetration enhancer, where the composition is formulated as a gel. In another embodiment, the composition comprises about 0.75% w/w erlotinib hydrochloride, about 70% w/w DMSO, about 25% w/w propylene glycol, about 0.5% w/w 2-phenoxyethanol, about 0.25% w/w methylparaben and about 3% w/w Carbopol 980, and the composition is formulated as a gel.

In one embodiment, there is provided a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w tapinarof and from about 10% to about 98% w/w at least one penetration enhancer.

In one embodiment, there is provided a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w tofacitinib citrate and from about 10% w/w to about 98% w/w at least one penetration enhancer.

In one embodiment, there is provided a topical composition for treatment, prevention or alleviation of a hyperkeratinization disorder in a patient in need thereof, comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w apremilast and from about 10% w/w to about 98% w/w at least one penetration enhancer.

In some embodiments, there is provided an injectable composition for treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa comprising at least one EGFR inhibitor selected from the group consisting of erlotinib, gefitinib, lapatinib, cetuximab, panitumumab, vandetanib, necitumumab, osimertinib and combinations thereof.

In another embodiment, the concentration of the EGFR inhibitor in the injectable composition is from about 0.01% to about 1%, from about 1% to about 3%, from about 3% to about 5% w/w, from about 5% to about 10% w/w or from about 10% to about 20% w/w.

In one embodiment, the injectable composition further comprises at least one solvent as described hereinabove.

In one embodiment, the injectable composition further comprises at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w.

In one embodiment, the injectable composition further comprises at least one additional second active agent (in addition to the EGFR inhibitor and the first active agent, or as combination with the EGFR inhibitor) co selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3% or from about 3% to about 5% w/w.

In some embodiments, the injectable composition further comprises (i) at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w; and (ii) comprises at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3% or from about 3% to about 5% w/w.

In some embodiments, there is provided a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a therapeutically effective amount of the composition as described hereinabove. In one embodiment, the composition comprises at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w. In one embodiment, the composition is topical.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of
(i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and
(ii) a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w, wherein the two separate compositions are administered concomitantly or sequentially, in either order.

In some embodiments, the compositions are topical compositions.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a composition comprising:
(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and
(ii) at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w.

In some embodiments, the composition is a topical composition.

In another embodiment, the method further comprises administering a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of
(i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and
(ii) a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof; in a concentration of from about 0.01% to about 1%, from about 1% to about 3%, from about 3% to about 5% w/w,
wherein the two separate compositions are administered concomitantly or sequentially, in either order. In some embodiments, the compositions are topical compositions.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a composition comprising:
(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w; and
(ii) at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof; in a concentration of from about 0.01% to about 1%, from about 1% to about 3%, from about 3% to about 5% w/w.

In some embodiments, the composition is a topical composition.

In another embodiment, the method further comprises administering a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of
(i) a composition comprising a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w;
(ii) a composition comprising at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w; and
(iii) a composition comprising at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof in a concentration of from about 0.01% to about 1%, from about 1% to about 3%, from about 3% to about 5% w/w;
wherein the three separate compositions are administered concomitantly or sequentially, in either order.

In some embodiments, the compositions are topical compositions.

In one additional embodiment, this invention is directed to a method of treatment, prevention or alleviation of a skin or mucosal disorder selected from the group consisting of psoriasis, palmoplantar psoriasis, acquired palmoplantar keratosis, eczema, ichthyosis vulgaris, non-melanoma skin cancer, actinic keratosis, a keratinization skin disorder, a keratinization mucosal disorder, pachyonychia congenita, hidradenitis suppurativa, Gorlin syndrome, prurigo nodularis and prurigo pigmentosa by topical or injectable administration to a subject in need thereof of a composition comprising:
(i) a therapeutically effective amount of at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w;
(ii) at least one additional first active agent selected from a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, from about 3% to about 5% w/w; and
(iii) at least one additional second active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3%, from about 3% to about 5% w/w.

In some embodiments, the composition is a topical composition.

In one embodiment, the at least one EGFR inhibitor and at least one additional first and/or second active agent within the above methods exhibit an additive or synergistic effect.

In some embodiments, the skin or mucosal disorder treated, prevented or alleviated within the methods described hereinabove is psoriasis.

In some embodiments, the skin or mucosal disorder treated, prevented or alleviated within the methods described hereinabove is palmoplantar psoriasis.

In some embodiments, the skin or mucosal disorder treated, prevented or alleviated within the methods described hereinabove is selected from a keratinization skin disorder and a keratinization mucosal disorder. In another embodiment, the keratinization skin disorder is hyperkeratinization skin disorder.

In another embodiment, the method of treating, preventing or alleviating hyperkeratinization disorder comprises topical administration to a subject in need thereof of a therapeutically effective amount of a topical composition comprising from about 0.1% w/w to about 1% w/w, from about 1% w/w to about 3% w/w, from about 3% w/w to about 5% w/w or from about 5% w/w to about 10% w/w erlotinib hydrochloride and from about 10% to about 98% w/w at least one penetration enhancer.

In another embodiment, the method of treating, preventing or alleviating hyperkeratinization disorder comprises topical administration to a subject in need thereof of a therapeutically effective amount of a topical composition comprising about 0.75% w/w erlotinib hydrochloride, about 70% w/w DMSO, about 25% w/w propylene glycol, about 0.5% w/w 2-phenoxyethanol, about 0.25% w/w methylparaben and about 3% w/w Carbopol 980, wherein the composition is formulated as a gel.

In another embodiment, the method of treating, preventing or alleviating hyperkeratinization disorder comprises topical administration to a subject in need thereof of a therapeutically effective amount of a topical composition comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w, from about 3% w/w to about 5% w/w tapinarof and from about 10% to about 98% w/w at least one penetration enhancer.

In another embodiment, the method of treating, preventing or alleviating hyperkeratinization disorder comprises topical administration to a subject in need thereof of a therapeutically effective amount of a topical composition comprising from about 0.1% w/w to about 1% w/w, from about 1% w/w to about 3% w/w, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w tofacitinib citrate and from about 10% to about 98% w/w at least one penetration enhancer.

In another embodiment, the method of treating, preventing or alleviating hyperkeratinization disorder comprises topical administration to a subject in need thereof of a therapeutically effective amount of a topical composition comprising from about 0.1% w/w to about 1% w/w, from about 1% w/w to about 3%, from about 3% w/w to about 5% w/w or from about 5% w/w to about 10% w/w erlotinib hydrochloride, from about 0.01% w/w to about 1% w/w, from about 1% w/w to about 3% w/w or from about 3% w/w to about 5% w/w apremilast and from about 10% w/w to about 98% w/w at least one penetration enhancer.

In some embodiments, the methods as described hereinabove do not induce or induces reduced cutaneous side-effects as compared with the same EGFR inhibitor amount administered in different methods/routes.

In some embodiments, the hyperkeratinization disorder treated, prevented or alleviated within the methods described hereinabove—is selected from palmoplantar psoriasis, hereditary palmoplantar keratoderma, acquired palmoplantar keratoderma, hydradenitis suppurativa, dermatitis, ichthyosis vulgaris, hereditary ichthyosis, acquired ichthyosis, actinic keratosis, a keratinization skin disorder and a keratinization mucosal disorder, pachyonychia congenita, hidradenitis suppurativa, Gorlin syndrome, prurigo nodularis, prurigo pigmentosa, nail psoriasis, non-melanoma skin cancer and precancerous skin, mucosal and nail lesions.

According to some embodiments, there is provided a method of treatment, prevention or alleviation of a skin disorder selected from the group consisting of psoriasis, palmoplantar psoriasis, acquired palmoplantar keratosis, eczema, ichthyosis vulgaris, non-melanoma skin cancer, actinic keratosis, pachyonychia congenita, hidradenitis suppurativa, Gorlin syndrome, prurigo nodularis and prurigo pigmentosa by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising at least one additional active agent selected from menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3, a corticosteroid, calcipotriene, tapinarof and combinations thereof in a concentration of from about 0.01% to about 1%, from about 1% to about 3%, from about 3% to about 5% w/w, wherein the at least one EGFR inhibitor and the at least one additional active agent selected from a corticosteroid, calcipotriene, tapinarof and combinations thereof exhibit an additive or synergistic effect.

According to some embodiments, there is provided a method of treatment of a skin or mucosal disorder selected from the group consisting of psoriasis, palmoplantar psoriasis, non-acquired palmoplantar keratosis, eczema, ichthyosis vulgaris, melanoma skin cancer, actinic keratosis, pachyonychia congenita, hidradenitis suppurativa, Gorlin syndrome, prurigo nodularis and prurigo pigmentosa by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising at least one additional active agent selected from a corticosteroid, calcipotriene, tapinarof and combinations thereof in a concentration of from about 0.01% to about 1%, from about 1% to about 3%, from about 3% to about 5% w/w, wherein said at least one EGFR inhibitor and said at least one additional active agent exhibit an additive or synergistic effect.

According to some embodiments, there is provided a method of treatment of psoriasis by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising at least one additional active agent selected from a corticosteroid, calcipotriene, tapinarof and combinations thereof, in a concentration of from about 0.01% to about 1%, from about 1% to about 3%, from about 3% to about 5% w/w, wherein said at least one EGFR inhibitor and said at least one additional active agent exhibit an additive or synergistic effect.

According to some embodiments, there is provided a method of treatment of a skin disorder selected from the group consisting of psoriasis, palmoplantar psoriasis, acquired palmoplantar keratosis, eczema, ichthyosis vulgaris, non-melanoma skin cancer, actinic keratosis, pachyonychia congenita, hidradenitis suppurativa, Gorlin syndrome, prurigo nodularis and prurigo pigmentosa by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising tapinarof in a concentration of from about 0.01% to about 1%, from about 1% to about 3% or from about 3% to about 5% w/w, wherein said at least one EGFR inhibitor and tapinarof exhibit an additive or synergistic effect.

According to some embodiments, there is provided a method of treatment of palmoplantar psoriasis by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising tapinarof in a concentration of from about 0.01% to about 1%, from about 1% to about 3% or from about 3% to about 5% w/w, wherein said at least one EGFR inhibitor and tapinarof exhibit an additive or synergistic effect.

According to some embodiments, there is provided a method any one of treatment of palmoplantar psoriasis by topical administration to a subject in need thereof a therapeutically effective amount of a composition comprising a EGFR inhibitor wherein the EGFR inhibitor is erlotinib in a concentration of from about 0.01% to about 1%, from about 1% to about 3%, from about 3% to about 5% w/w, from about 5% to about 10% w/w or from about 10% to about 20% w/w, further comprising tapinarof in a concentration of from about 0.01% to about 1%, from about 1% to about 3% or from about 3% to about 5% w/w, wherein erlotinib and tapinarof exhibit an additive or synergistic effect.

According to some embodiments, there is provided a method of treatment of a skin or mucosal disorder, wherein the skin or mucosal disorder is selected from a keratinization skin disorder and a keratinization mucosal disorder by topical administration to a subject in need thereof a therapeutically effective amount of a composition comprising at least one EGFR inhibitor selected from the group consisting of erlotinib, gefitinib, lapatinib, cetuximab, panitumumab, vandetanib, necitumumab, osimertinib and combinations thereof, in a concentration of from about 0.01% to about 1%, from about 1% to about 3%, from about 3% to about 5% w/w, from about 5% to about 10% w/w or from about 10% to about 20% w/w, further comprising tapinarof in a concentration of from about 0.01% to about 1%, from about 1% to about 3% or from about 3% to about 5% w/w, wherein said at least one EGFR inhibitor and tapinarof exhibit an additive or synergistic effect.

According to some embodiments, there is provided a method of treatment of a keratinization skin disorder or a keratinization mucosal disorder by topical administration to a subject in need thereof a therapeutically effective amount of a composition comprising a EGFR inhibitor wherein the EGFR inhibitor is erlotinib in a concentration of from about 0.01% to about 1%, from about 1% to about 3%, from about 3% to about 5% w/w, from about 5% to about 10% w/w or from about 10% to about 20% w/w, further comprising tapinarof in a concentration of from about 0.01% to about 1%, from about 1% to about 3% or from about 3% to about 5% w/w, wherein erlotinib and tapinarof exhibit an additive or synergistic effect.

In some embodiments, there is provided a method of treatment comprising once or twice daily application of therapeutically effective amounts of the composition or the two or three separate compositions to the skin portion of the subject affected by the said skin or mucosal disorder until the skin or mucosal disorder is cured, prevented or alleviated or according to doctor's instructions. In one embodiment, the method comprises once or twice daily topical application of therapeutically effective amounts of the topical composition or the two or three separate topical compositions to the skin portion of the subject affected by the said skin or mucosal disorder until the skin or mucosal disorder is cured, prevented or alleviated or according to doctor's instructions.

In one embodiment, the administration of the compositions within the above methods is topical or injectable administration (subcutaneous, intramuscular, intravenous, intraperitoneal, intracardiac, intraarticular, intracavernous or intralesional administration, each represents a separate embodiment) intramuscular, intravenous, intraperitoneal, intracardiac, intraarticular, intracavernous or intralesional administration, each represents a separate embodiment). In another embodiment, the administration is topical or intralesional. In another embodiment, intralesional administration is done by regular injections or subcutaneous injections with microneedles. In another embodiment, the compositions are topical or injectable. Each possibility represents a separate embodiment of this invention.

In some other embodiments, the EGFR inhibitor in any of the methods and compositions of this invention is erlotinib or salt thereof. In another embodiment the EGFR inhibitor is Erlotinib HCl.

As EGFR inhibitors in general and erlotinib in particular are poorly soluble, the compositions of this invention need to comprise a high EGFR inhibitor concentration of up to 20% w/w. The compositions are in the form of partly solubilized suspensions and may comprise organic solvents and solubility enhancers as well as other ingredients (e.g. penetration enhancer) and active agents which are all described hereinabove. In one embodiment, the at least one EGFR inhibitor is partly or entirely solubilized.

Unexpectedly, it was found that within the compositions of this invention, EGFR inhibitors were at least partially solubilized and used in solution/suspension form, thus the inhibitors could be used in topical or injectable compositions. Further, it was found that the compositions of this invention, when administered topically or intralesional injected within the methods described hereinabove—do not induce or induces reduced cutaneous side-effects as compared with the same EGFR inhibitor amount administered in different methods/routes.

Definitions

As used herein, the terms "pharmaceutically active agent" or "active agent" or "active pharmaceutical ingredient" or "API" are interchangeable and mean the ingredient is a pharmaceutical drug which is biological active and is regulatory approved or approvable as such.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to this invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprise", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Example 1

Preparation and Stability of a 0.75% Topical Erlotinib HCl Gel Composition 0.75% erlotinib; 70% DMSO;
Composition:

| Ingredient | % in formulation |
|---|---|
| Erlotinib hydrochloride | 0.75 |
| DMSO | 70 |
| Propylene glycol | 25.50 |
| 2-phenoxyethanol | 0.5 |
| Methylparaben | 0.25 |
| Carbopol 980 | 3 |

Procedure:
Erlotinib hydrochloride was dissolved in DMSO at 40° C.
Methylparaben was added under stirring
Carbopol was added under stirring
2-phenoxyethanol was dissolved in propylene glycol and added
The formulation was stirred and homogenized to obtain a homogeneous gel.
Stability Results

| | Time zero | 1 month at 40 C. | 2 months at 40 C. | 3 months at 40 C. |
|---|---|---|---|---|
| Erlotinib assay | 0.70% | 0.71% | 0.71% | 0.73% |

Example 2

Preparation and Stability of a 0.5% Topical Erlotinib HCl Gel Composition 0.5% erlotinib; 70% DMSO;
Composition:

| Ingredient | % in formulation |
|---|---|
| Erlotinib hydrochloride | 0.5 |
| DMSO | 70 |
| Propylene glycol | 25.75 |
| 2-phenoxyethanol | 0.5 |

-continued

| Ingredient | % in formulation |
|---|---|
| Methylparaben | 0.25 |
| Carbopol 980 | 3 |

Procedure:

Erlotinib hydrochloride was dissolved in DMSO at 40° C.
Methylparaben was added under stirring
Carbopol was added under stirring
2-phenoxyethanol was dissolved in propylene glycol and added
The formulation was stirred and homogenized to obtain a homogeneous gel.

Stability Results

|  | Time zero | 2 months at 40 C. | 3 months at 40 C. |
|---|---|---|---|
| Erlotinib assay | 0.46% | 0.47% | 0.46% |

Example 3

Preparation and Stability of a 0.5% Topical Erlotinib HCl Gel Composition 0.5% erlotinib; 45.5% DMSO
Composition:

| Ingredient | % in formulation |
|---|---|
| Erlotinib hydrochloride | 0.5 |
| DMSO | 45.5 |
| Propylene glycol | 50.25 |
| 2-phenoxyethanol | 0.5 |
| Methylparaben | 0.25 |
| Carbopol 980 | 3 |

Procedure:

Erlotinib hydrochloride was dissolved in DMSO at 40° C.
Methylparaben was added under stirring
Carbopol was added under stirring
2-phenoxyethanol was dissolved in propylene glycol and added
The formulation was stirred and homogenized to obtain a homogeneous gel.

Stability Results

|  | Time zero | 2 months at 40 C. | 3 months at 40 C. |
|---|---|---|---|
| Erlotinib assay | 0.47% | 0.47% | 0.46% |

Example 4

Preparation and Stability of a 0.5% Topical Erlotinib HCl Gel Composition 0.5% erlotinib; 50% EtOH 70%
Composition:

| Ingredient | % in formulation |
|---|---|
| Erlotinib hydrochloride | 0.5 |
| EtOH 70% | 50 |
| Propylene glycol | 46.25 |
| 2-phenoxyethanol | 0.5 |
| Methylparaben | 0.25 |
| Carbopol 980 | 2.5 |

Procedure:

Erlotinib hydrochloride was dissolved in EtOH at 40° C.
Methylparaben was added under stirring
Carbopol was added under stirring
2-phenoxyethanol was dissolved in propylene glycol and added
The formulation was stirred and homogenized to obtain a homogeneous gel.

Stability Results

|  | Time zero | 2 weeks at 40 C. |
|---|---|---|
| Erlotinib assay | 0.47% | 0.48% |

Example 5

Preparation and Stability of a 1.25% Topical Erlotinib HCl Gel Composition 1.25% erlotinib; 95% DMSO;
Composition:

| Ingredient | % in formulation |
|---|---|
| Erlotinib hydrochloride | 1.25 |
| DMSO | 95 |
| 2-phenoxyethanol | 0.5 |
| Methylparaben | 0.25 |
| Carbopol 980 | 3 |

Procedure

Erlotinib hydrochloride was dissolved in DMSO at 40° C.
Methylparaben was added under stirring.
Carbopol was added under stirring.
2-phenoxyethanol was dissolved in propylene glycol and added
The formulation was stirred and homogenized to obtain a homogeneous gel.

Example 6

Preparation and Stability of a 1% Topical Erlotinib HCl Gel Composition

1% erlotinib; 49% PEG-400; 30% PEG-3350
Composition:

| Ingredient | % in formulation |
| --- | --- |
| Erlotinib hydrochloride | 1 |
| Propylene glycol | 20 |
| PEG-400 | 49 |
| PEG-3350 | 30 |

Procedure:
Propylene glycol, PEG-400 and PEG-3350 were stirred at 70% to obtain a homogeneous liquid
Erlotinib hydrochloride was added under stirring
Carbopol was added under stirring and homogenization
2-phenoxyethanol was dissolved in propylene glycol and added
The formulation was cooled to room temperature.

Example 7

Preparation and Stability of a 1% Erlotinib HCl+1% Tapinarof Topical Gel Composition

| Ingredient | % in formulation |
| --- | --- |
| Erlotinib hydrochloride | 1 |
| Tapinarof | 1 |
| DMSO | 70 |
| Propylene glycol | 24.25 |
| 2-phenoxyethanol | 0.5 |
| Methylparaben | 0.25 |
| Carbopol 980 | 3 |

Procedure:
Erlotinib hydrochloride is dissolved in DMSO at 40° C.
Tapinarof is added under stirring
Methylparaben is added under stirring
Carbopol is added under stirring
2-phenoxyethanol is dissolved in propylene glycol and added
The formulation is stirred and homogenized to obtain a homogeneous gel.

Example 8

Preparation of a 1% Erlotinib HCl+0.5% Tofacitinib Citrate Topical Gel Composition

| Ingredient | % in formulation |
| --- | --- |
| Erlotinib hydrochloride | 1 |
| tofacitinib citrate | 0.5 |
| DMSO | 70 |
| Propylene glycol | 24.75 |
| 2-phenoxyethanol | 0.5 |
| Methylparaben | 0.25 |
| Carbopol 980 | 3 |

Procedure:
Erlotinib hydrochloride is dissolved in DMSO at 40° C.
Tofacitinib citrate is added under stirring
Methylparaben is added under stirring
Carbopol is added under stirring
2-phenoxyethanol is dissolved in propylene glycol and added
The formulation is stirred and homogenized to obtain a homogeneous gel.

Example 9

Preparation of a 1% Erlotinib HCl+0.5% Apremilast Topical Gel Composition

| Ingredient | % in formulation |
| --- | --- |
| Erlotinib hydrochloride | 1 |
| Apremilast | 0.5 |
| DMSO | 70 |
| Propylene glycol | 24.75 |
| 2-phenoxyethanol | 0.5 |
| Methylparaben | 0.25 |
| Carbopol 980 | 3 |

Procedure:
Erlotinib hydrochloride is dissolved in DMSO at 40° C.
Apremilast is added under stirring
Methylparaben is added under stirring
Carbopol is added under stirring
2-phenoxyethanol is dissolved in propylene glycol and added
The formulation is stirred and homogenized to obtain a homogeneous gel.

What is claimed is:

1. A method of treatment or alleviation of psoriasis by topical administration to a subject in need thereof of a composition comprising a therapeutically effective amount of erlotinib, or a pharmaceutically acceptable salt thereof, in a concentration of from about 3% to about 5% w/w or from about 5% to about 10% w/w.

2. A method of treatment or alleviation of psoriasis by topical administration to a subject in need thereof of a composition comprising:
   (i) a therapeutically effective amount of erlotinib, or a pharmaceutically acceptable salt thereof, in a concentration of from about 3% to about 5% w/w or from about 5% to about 10% w/w; and
   (ii) at least one additional active agent selected from the first active agent group consisting of a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, or from about 3% to about 5% w/w.

3. The method of claim 2, wherein the method further comprises administering a composition comprising at least one additional active agent selected from the second active agent group consisting of menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3%, or from about 3% to about 5% w/w, wherein the two separate compositions are administered concomitantly or sequentially, in either order.

4. A method of treatment or alleviation of psoriasis by topical administration to a subject in need thereof of a composition comprising:
(i) a therapeutically effective amount of erlotinib, or a pharmaceutically acceptable salt thereof, in a concentration of from about 3% to about 5% w/w or from about 5% to about 10% w/w; and
(ii) at least one additional active agent selected from the second active agent group consisting of menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3%, from about 3% to about 5% w/w.

5. The method of claim 4, wherein the method further comprises administering a composition comprising at least one additional active agent selected from the first active agent group consisting of a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, or from about 3% to about 5% w/w.

6. A method of treatment or alleviation of psoriasis by topical administration to a subject in need thereof of a composition comprising:
(i) a therapeutically effective amount of erlotinib, or a pharmaceutically acceptable salt thereof, in a concentration of from about 3% to about 5% w/w or from about 5% to about 10% w/w;
(ii) at least one additional active agent selected from the first active agent group consisting of a corticosteroid, calcipotriene, tapinarof, a Janus kinase inhibitor (JAK inhibitor), a phosphodiesterase-4 inhibitor (PDE4 inhibitor), and combinations thereof, in a concentration of from about 0.01% to about 1%, from about 1% to about 3%, or from about 3% to about 5% w/w; and
(iii) at least one additional active agent selected from the second active agent group consisting of menadione, ketoconazole, dapsone, cevimeline, spironolactone, tretinoin, pimecrolimus, a tetracycline, a sunscreen, doxycycline, epidermal growth factor (EGF), lycopene, threolone, synthomycine, erythromycin, Vitamin K3 and combinations thereof, in a concentration of from about 0.01% to about 1%, from about 1% to about 3%, or from about 3% to about 5% w/w.

7. The method of claim 1, wherein said composition is a topical composition comprising from about 3% w/w to about 5% w/w or from about 5% w/w to about 10% w/w erlotinib or erlotinib hydrochloride and from about 10% to about 98% w/w at least one penetration enhancer.

8. The method of 2, wherein said composition is a topical composition comprising from about 3% w/w to about 5% w/w or from about 5% w/w to about 10% w/w erlotinib or erlotinib hydrochloride and from about 10% to about 98% w/w at least one penetration enhancer.

9. The method of 4, wherein said composition is a topical composition comprising from about 3% w/w to about 5% w/w or from about 5% w/w to about 10% w/w erlotinib or erlotinib hydrochloride and from about 10% to about 98% w/w at least one penetration enhancer.

10. The method of 6, wherein said composition is a topical composition comprising from about 3% w/w to about 5% w/w or from about 5% w/w to about 10% w/w erlotinib or erlotinib hydrochloride and from about 10% to about 98% w/w at least one penetration enhancer.

11. The method of claim 1, wherein the method does not induce or induces reduced cutaneous side-effects as compared with systemic administration of the same amount of erlotinib, or of the pharmaceutically acceptable salt thereof.

12. The method of claim 2, wherein the method does not induce or induces reduced cutaneous side-effects as compared with systemic administration of the same amount of erlotinib, or the pharmaceutically acceptable salt thereof.

13. The method of claim 4, wherein the method does not induce or induces reduced cutaneous side-effects as compared with systemic administration of the same amount of erlotinib, or the pharmaceutically acceptable salt thereof.

14. The method of claim 6, wherein the method does not induce or induces reduced cutaneous side-effects as compared with systemic administration of the same amount of erlotinib, or the pharmaceutically acceptable salt thereof.

15. The method of claim 1, wherein the method comprises once or twice daily topical application of therapeutically effective amounts of the said composition to the skin portion of the subject affected by said psoriasis until the skin is cured or alleviated or according to doctor's instructions.

16. The method of claim 2, wherein the method comprises once or twice daily topical application of therapeutically effective amounts of the said composition to the skin portion of the subject affected by said psoriasis until the skin is cured or alleviated or according to doctor's instructions.

17. The method of claim 4, wherein the method comprises once or twice daily topical application of therapeutically effective amounts of the said composition to the skin portion of the subject affected by the psoriasis until the skin is cured or alleviated or according to doctor's instructions.

18. The method of claim 6, wherein the method comprises once or twice daily topical application of therapeutically effective amounts of the said composition to the skin portion of the subject affected by said psoriasis until the skin is cured or alleviated or according to doctor's instructions.

19. The method of claim 2, wherein said composition is a topical composition comprising from about 3% w/w to about 5% w/w or from about 5% w/w to about 10% w/w erlotinib or erlotinib hydrochloride, from about 0.01% w/w to about 1% w/w, from about 1% w/w to about 3% w/w, or from about 3% w/w to about 5% w/w tapinarof and from about 10% to about 98% w/w at least one penetration enhancer.

20. The method of claim 2, wherein said composition is a topical composition comprising from about 3% w/w to about 5% w/w or from about 5% w/w to about 10% w/w erlotinib or erlotinib hydrochloride, from about 0.01% w/w to about 1% w/w, from about 1% w/w to about 3% w/w or from about 3% w/w to about 5% w/w tofacitinib citrate and from about 10% to about 98% w/w at least one penetration enhancer.

21. The method of claim 2, wherein said composition is a topical composition comprising from about 3% w/w to about 5% w/w or from about 5% w/w to about 10% w/w erlotinib or erlotinib hydrochloride, from about 0.01% w/w to about 1% w/w or from about 1% w/w to about 3% w/w roflumilast and from about 10% w/w to about 98% w/w at least one penetration enhancer.

* * * * *